United States Patent [19]

Rosentreter et al.

[11] Patent Number: 4,469,696

[45] Date of Patent: Sep. 4, 1984

[54] SUBSTITUTED 2-AMINO-PYRIDINE DERIVATIVE COMPOUNDS, THEIR PRODUCTION AND THEIR MEDICINAL USE

[75] Inventors: Ulrich Rosentreter; Walter Puls; Hilmar Bischoff, all of Wuppertal, Fed. Rep. of Germany

[73] Assignee: Bayer Aktiengesellschaft, Leverkusen, Fed. Rep. of Germany

[21] Appl. No.: 384,469

[22] Filed: Jun. 3, 1982

[30] Foreign Application Priority Data

Jun. 24, 1981 [DE] Fed. Rep. of Germany ........ 3124673

[51] Int. Cl.$^3$ .................. C07D 401/00; A61K 31/495
[52] U.S. Cl. ..................................... 424/250; 544/360; 544/124; 544/126; 544/127; 544/128; 544/283; 544/304; 546/95; 546/146; 546/153; 546/257; 546/275; 546/278; 546/280; 546/281; 546/283; 546/284; 546/304; 546/311; 546/312; 424/249; 424/251; 424/257; 424/258; 424/263

[58] Field of Search ....................... 544/360, 283, 304; 424/250

[56] References Cited

FOREIGN PATENT DOCUMENTS 013153 7/1980 European Pat. Off. ............ 546/193
2949701 6/1981 Fed. Rep. of Germany ...... 544/360

OTHER PUBLICATIONS

Neunhoeffer, H., et al., Chemische Berichte, 111, 299-308, 1978.

*Primary Examiner*—Donald G. Daus
*Assistant Examiner*—S. A. Gibson
*Attorney, Agent, or Firm*—Sprung, Horn, Kramer & Woods

[57] ABSTRACT

The invention relates to 4-,5-and 6-substituted 2-amino pyridines of Formula (I) and methods for their preparation. Also included in the invention are compositions containing said 2-amino pyridines of Formula (I) and the use of said compounds and compositions for use inter alia, as lipid absorption inhibitors.

12 Claims, No Drawings

SUBSTITUTED 2-AMINO-PYRIDINE DERIVATIVE COMPOUNDS, THEIR PRODUCTION AND THEIR MEDICINAL USE

The present invention relates to certain 2-amino-pyridine derivative compounds substituted in the 4-, 5- and 6-position, to a process for their production and to their use as lipid absorption inhibitors.

Pyridine derivatives with a hypolipaemic action are already known (see European Published Application No. 0,013,153). With a knowledge of the state of the art, it could not have been foreseen that pyridine derivatives which carry a nitrogen-containing radical in the 2-position and are also substituted in the 4-, 5- and 6-position would possess an advantageous lipid absorption-inhibiting action.

According to the present invention there are provided compounds which are substituted 2-amino-pyridine derivatives of the formula

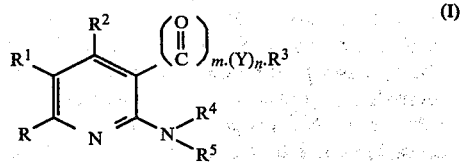

or a salt thereof,
in which R represents an alkyl group which is optionally substituted by hydroxyl, aryl or aralkyl, by a radical of the formula

wherein R' and R" are identical or different and each denotes a hydrogen atom, an alkyl or aralkyl group, by aralkyl or by aryl each of which is optionally substituted on the aryl moiety by 1 or 2 identical or different substituents selected from halogen, alkly, alkoxy, alkylmercapto or trifluoromethyl, or R and $R^1$ together complete a fused (preferably 5- or 6-membered) carbocyclic ring, which is optionally substituted particularly mono- or di-substituted by hydroxyl, halogen, nitro, alkoxy or a group of formula (Ia), as defined above,
and to which carbocyclic ring an aryl (particularly monocyclic carbocyclic aryl) ring can be fused, the aryl ring optionally being substituted by 1 or 2 identical or different substitutents selected from halogen, alkyl, alkoxy, alkylmercapto or trifluoromethyl, and optionally being interrupted by oxygen, sulphur or a group of the general formula $NR^6$,
wherein $R^6$ has a meaning given for $R^1$ and $R^2$, and $R^2$ represents, or $R^1$ and $R^2$ which are identical or different each represent, an alkyl group which is optionally substituted by (preferably mono- or bi-cyclic carbocyclic) aryl, heteroaryl, hydroxyl, halogen, alkoxy, carboxy, cyano, carbalkoxy or a group of the formula

wherein
$R^4$ and $R^5$ have the meanings given below, or by a (preferably mono- or bi-cyclic carbocyclic) aryl radical or a heteroaryl radical selected from thienyl, furyl, pyrryl, pyrazolyl, imidazolyl, oxazolyl, isooxazolyl, thiazolyl, pyridyl, pyridazinyl, pyrimidyl, pyrazinyl, quinolyl, isoquinolyl, indolyl, benzimidazolyl, quinazolyl and quinoxalyl, the aryl radical or heteroaryl radical optionally containing 1, 2 or 3 identical or different substituents selected from phenyl, alkyl, alkenyl, alkinyl, alkoxy, alkenoxy, alkinoxy, alkylene, dioxyalkylene, halogen, acyloxy, trifluoromethylthio, trifluoromethyl, trifluoromethoxy, hydroxyl, a group of the formula (Ib), as defined above, nitro, cyano, azido, carboxyl, carbalkoxy, carboxamido, sulphonamido and $SO_m$-alkyl (in which m is 0, 1 or 2), and the alkyl and alkoxy substituents in turn optionally being substituted by hydroxyl, alkoxy, carboxyl, carbalkoxy, halogen, a group of formula (Ib), as defined above, aroyloxy or alkanoyloxy, the aroyl and alkanoyl radicals in turn optionally being substituted by hydroxyl, alkoxy, halogen, carboxyl or carbalkoxy, and m and n are identical or different and each denotes 0 or 1, and Y represents oxygen, a group $SO_{m'}$ (in which m' is 0, 1 or 2) or a group of the formula $N-R^6$, wherein $R^6$ denotes an alkyl or aryl group, and $R^3$ represents a hydrogen atom or an alkyl group which is optionally substituted by hydroxyl, epoxy, alkoxy, halogen, a group of formula (Ib), as defined above, a carboxyl, carbalkoxy, cyano or alkenyl group or an aryl group which is optionally substituted by 1 or 2 identical or different substituents selected from hydroxyl, alkoxy, halogen, alkyl, alkenyl, aryl, alkylmercapto, alkylamino, carboxyl, carbalkoxy, cyano, trifluoromethyl, trifluoromethoxy and trifluoromethylthio, and $R^4$ and $R^5$ are identical or different and each represents a hydrogen atom, an alkyl, alkenyl or alkinyl group (the alkyl and alkenyl groups being straightchain, branched or cyclic and optionally substituted by the group $COR^{5'}$, wherein $R^{5'}$ denotes alkyl, aralkyl or aryl), or $R^4$ and $R^5$, together with the nitrogen atom, form a 4-membered to 7-membered ring which is optionally interrupted by oxygen, sulphur, an NH group or a group of the formula $NR^{6'}$, wherein $R^{6'}$ has a meaning given above for $R^1$ and $R^2$.

According to the present invention there is further provided a process for the production of a compound of the invention in which a 2-amino-3,4-dihydropyridine derivative of the formula

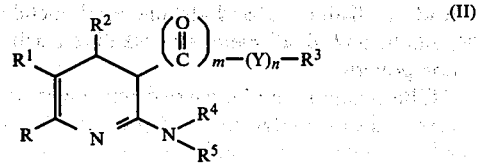

in which R, $R^1$, $R^2$, $R^3$, $R^4$, $R^5$, Y, m and n have the meaning given above,
is oxidised by oxygen in the presence of an inert, organic solvent and a basic catalyst, and the product of formula (I) is converted, if desired, into a salt thereof.

If, 4,5-bis-(4-methoxyphenyl)-6-methyl-2-(4-phenylpiperazino)-3,4-dihydropyridine is used, the course of the reaction according to the present invention is illustrated by the following equation:

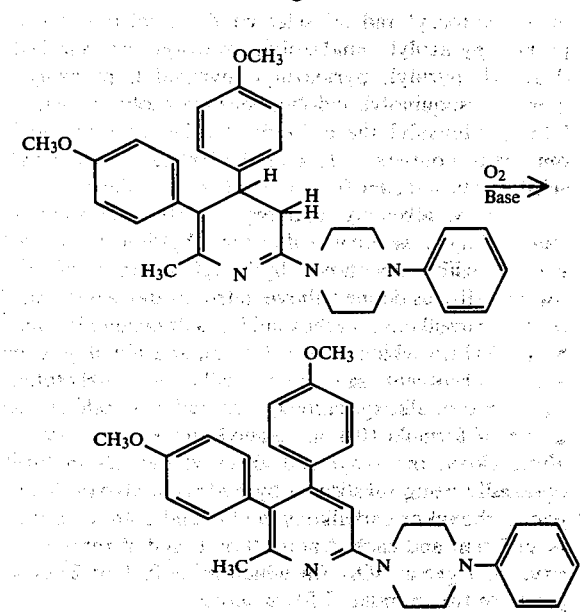

The 2-amino-3,4-dihydro-pyridine derivatives, of the general formula (II), which can be used as starting compounds are known or can be prepared according to known methods (see DE-OS (German Published Specification) No. 2,949,701).

In carrying out the process according to the invention, any of the inert organic solvents are suitable as the diluent. These preferably include $C_1$ to $C_4$ alcohols (such as methanol, ethanol or propanol), ethers (such as tetrahydrofuran, dioxane, diethyl ether or 1,2-dimethoxyethane), ketones (such as acetone), pyridine, dimethylformamide, dimethylsulphoxide, hexamethylphosphoric acid triamide or acetonitrile.

The reaction temperatures can be varied within a relatively wide range. In general, the reaction is carried out at a temperature between −80° C. and 100° C., preferably between −30° C. and 40° C.

The following may be preferably mentioned as bases containing an alkali metal or alkaline earth metal which may be used as the basic catalysts: alkali metal and alkaline earth metal hydroxides and alcoholates (in particular alkali metal alcoholates, particularly alkanolates), alkali metal and alkaline earth metal amides, (in particular alkali metal amides), alkali metal and alkaline earth metal hydrides (in particular alkali metal hydrides), alkali metal and alkaline earth metal alkyl compounds, and alkali metal and alkaline earth metal aryl compounds.

The reaction can be carried out under normal pressure and also under elevated pressure. In general it is carried out under normal pressure.

The oxygen required for the oxidation can be fed in, in pure form or diluted with other inert gases, in particular nitrogen or argon. In general, atmospheric oxygen is used as the oxidising agent.

If not expressly stated to the contrary, in the present application "alkyl" represents straight-chain, branched or cyclic alkyl having up to 10 carbon atoms (preferably particular straight-chain or branched alkyl having up to 6 carbon atoms) and "alkoxy" represents straight-chain or branched alkoxy having 1 to 6 carbon atoms.

"Aryl" preferably denotes phenyl or naphthyl. "Aralkyl" preferably represents benzyl, phenethyl or phenylpropyl.

"Halogen" preferably denotes fluorine, chlorine or bromine.

Particularly preferred compounds according to the present invention are those in which R represents a straight-chain or branched alkyl group which has up to 6 carbon atoms (and which is optionally monosubstituted or disubstituted by hydroxyl, alkoxy having 1 to 4 carbon atoms, amino, monoalkylamino, dialkylamino or benzyl-alkylamino, the alkyl groups mentioned containing 1 to 4 carbon atoms), or a phenyl or benzyl radical (the phenyl ring being optionally monosubstituted or disubstituted by identical or different substituents selected from fluorine, chlorine, bromine, alkyl, alkoxy or alkylmercapto having 1 to 4 carbon atoms each, and trifluoromethyl), or R and $R^1$ together complete a fused carbocyclic ring to which a benzene or naphthalene ring is fused (the benzene or naphthalene ring being optionally monosubstituted or disubstituted by identical or different substituents selected from fluorine, chlorine, bromine, alkyl or alkoxy having 1 to 4 carbon atoms each, and trifluoromethyl, and optionally being interrupted by oxygen, sulphur, an NH group or an alkyl-substituted nitrogen atom having 1 to 4 carbon atoms in the alkyl group), and $R^2$ represents, or $R^1$ and $R^2$ which are identical or different each represent, a straight-chain or branched alkyl group which optionally carries 1 or 2 identical or different substituents selected from phenyl, hydroxyl, amino, carboxyl, halogen, alkylamino and dialkylamino), or an aromatic ring selected from phenyl, naphthyl, furyl and pyridyl, this aromatic ring optionally being substituted by 1 to 2 identical or different substituents selected from nitro, cyano, azido, hydroxyl, amino, carboxyl, halogen, phenyl, alkyl, alkoxy, trifluoromethyl, trifluoromethoxy, benzoyloxy, alkanoyloxy, trifluoromethylthio, alkylmercapto, alkylsulphonyl and alkylamino (the alkyl and alkoxy radicals mentioned each containing 1 to 4 carbon atoms, and in turn being optionally substituted by hydroxyl, alkoxy, aroyloxy, alkanoyloxy or a group of the general formula

in which $R^4$ and $R^5$ have the meanings given below, m and n are 0 or 1, and Y represents oxygen, sulphur or an NH group, and $R^3$ represents a hydrogen atom, a straight-chain or branched alkyl or alkenyl group which has up to 6 carbon atoms and is optionally substituted by hydroxyl, alkoxy, fluorine, chlorine, bromine, phenyl, carboxyl, carbalkoxy or a group of the general formula

in which $R^4$ $R^5$ have the meanings given below, or an aromatic ring selected from phenyl, furyl, pyridyl or naphthyl, this aromatic ring optionally containing 1 or 2 identical or different substituents selected from cyano, hydroxyl, amino, carboxyl, halogen, phenyl, alkyl, alkoxy, trifluoromethyl, trifluoromethoxy, trifluoromethylthio or alkylamino, the alkyl and alkoxy radicals mentioned each containing 1 to 4 carbon atoms, and $R^4$ and $R^5$ are identical or different and each represents a hydrogen atom or an alkyl or alkenyl group having up to 6 carbon atoms, the alkyl and alkenyl groups optionally being substituted by the group $COR^{5'}$, wherein $R^{5'}$ denotes an alkyl group having 1 to 4 carbon atoms or a benzyl or phenyl group, or $R^3$ and $R^4$, together with the nitrogen atom, form a 5-membered to 7-membered ring which is optionally interrupted by oxygen, sulphur, NH or $NR^6$, wherein $R^6$ has a meaning given immediately above for $R^1$ and $R^2$.

Particularly preferred compounds of the present invention are those in which

R represents an alkyl group having 1 to 4 carbon atoms, or a benzyl or phenyl group, $R^1$ and $R^2$ are identical or different and each represents a furyl, pyridyl or phenyl group, the phenyl ring optionally containing 1 or 2 identical or different substitents selected from fluorine, chlorine, nitro, cyano, amino, azido, trifluoromethyl, trifluoromethoxy, trifluoromethylthio, alkylmercapto, alkyl having 1 to 4 carbon atoms, alkoxy having 1 to 4 carbon atoms, phenyl and alkylamino having 1 or 2 carbon atoms per alkyl radical, $m_3$ and n are 0, $R^3$ represents a hydrogen atom, and $R^4$ and $R^5$ are identical or different and each represents a hydrogen atom or an alkyl group having 1 to 4 carbon atoms, or $R^4$ and $R^5$, together with the nitrogen atom, form a 5-membered or 6-membered ring which is optionally interrupted by the group NH or $NR^6$, wherein $R^6$ has a meaning given immediately above for $R^2$.

Surprisingly, the compounds according to the invention, of the formula (I), exhibit a very powerful action in the treatment of fat metabolism disorders. In particular, they cause a lowering of an elevated cholesterol level in the serum, and simultaneously reduce a hypertriglyceridaemia.

The compounds according to the invention are therefore advantageous for treating hyperlipoproteinaemias, arteriosclerosis and adiposity, and for treating metabolic irregularities caused by these.

The compounds according to the invention are particularly suitable as lipid absorption inhibitors, diuretics, saluretics, antiarrythmics and cardiotonics.

The diuretic and saluretic action was investigated on rats. For this purpose, male rats were used, and were given, after fasting, 10 ml/kg of liquid by means of a stomach tube. This liquid contained 0.5 tylosis as well as a particular dose of the test preparation (control animals without the test preparation). The urine eliminated was collected during 6 hours, and the sodium and potassium content was then determined photometrically, in the customary manner.

The antiarrythmic action of the compounds according to the invention was demonstrated, by means of standard test methods, by the effect on the refractory period of the myocardium. Therapeutic doses of antiarrythmics are known to prolong the refractory period of the myocardium. This prolongation of the refractory period and the determination of the contraction force in isolated myocardial preparations were effected according to known methods (see: Govier, J. Pharmacol, Exp. Ther. 148, 100–105, (1965) and Roseblueth et al., J. Cell Comp. Physiol. 33, 405–439 (1949)).

None of these actions has hitherto been disclosed for the substance class of the 2-amino-pyridines. It must therefore be regarded as particularly surprising that the compounds according to the invention possess these new and advantageous actions. As a novel class of substance for treating metabolic irregularities and cardiac irregularities, with simultaneously very good toleration, they represent an enrichment of pharmacy.

As stated above, the invention also relates to the use in medicine in combating diseases involving the fat metabolism of the compounds of the invention.

The present invention provides a pharmaceutical composition containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 700 mg to 15 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) an then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally. Preferred pharmaceutical compositions and medicaments are therefore those adapted for administration such as oral administration. Administration in the method of the invention is peferably oral administration.

In general it has proved advantageous to administer amounts of from 10 to 100 mg/kg, preferably 20 to 100 mg/kg, of body weight per day, distributed over 1 to 6 administrations and, in particular, before and/or during and/or after meals, to achieve effective results. An individual dose preferably contains the active compound or compounds in amounts of 10 to 100 mg/kg of body weight. Nevertheless, it can at times be necessary to deviate from those dosage rates, and in particular to do so as a function of the nature and body weight of the subjected to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered, as mentioned, it can be advisable to divide these into several individual administrations over the course of the day.

An example of the substance group according to the invention is that with an absorption-inhibiting action, supported by the following pharmacological data for the compounds of Examples 1 (b) and 5.

| Example No. | Dose mg/kg | Reduction in the liver cholesterol increase in comparison to the control after oral administration of cholesterol in % |
|---|---|---|
| 1b | 100 | 27.6% |
|  | 30 | 10.7% |
| 5 | 100 | 18.9 |

The following Examples illustrate processes for the production of compounds according to the present invention.

EXAMPLE 1

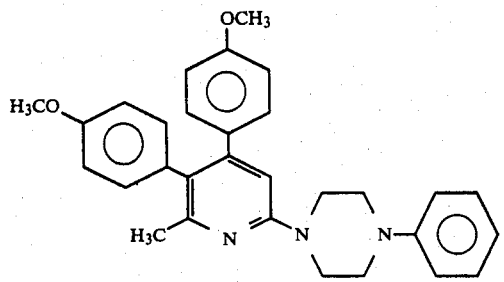

(a)

7 g (15 millimol) of 4,5-bis-(4-methoxyphenyl)-6-methyl-2-(4-phenylpiperazino)-3,4-dihydropyridine were suspended in 150 ml of analytically pure dimethylsulphoxide, whilst stirring, and 1.7 g (15 millimol) of potassium tert.-butylate were added to the suspension. The mixture was stirred in a closed vessel until a clear, orange-red coloration had formed. The reaction solution was then stirred in an open reaction flask for 1 hour. After the reaction solution had been neutralised with glacial acetic acid, the colourless precipitate which had separated out was filtered off under suction, washed with methanol and dried in vacuo to obtain 4,5-bis-(4-methoxyphenyl)-6-methyl-2-(4-phenyl-piperazino)-pyridine.

Yield 69% of theory, melting point: 173° to 174° C.

EXAMPLE 2

(b)

2.1 g (4.5 millimol) of 4,5-bis-(4-methoxyphenyl)-6-methyl-2-(4-phenylpiperazino)-3,4-pyridine were dissolved in 200 ml of absolute dichloromethane, and the solution was cooled to $-20°$ C. to $-30°$ C. 19 ml of a solution of 100 ml of boron tribromide in 300 ml of dichloromethane were added dropwise at this temperature, in the course of 1 hour The mixture was further stirred for 2 hours at $-20°$ C., and 30 ml of methoanol were then slowly added dropwise. The reaction solution was washed with saturated sodium bicarbonate solution, dried with sodium sulphate and concentrated by evaporating in vacuo. The resulting oily residue crystallised from methanol.

Yield: 84% of theory, melting point: 230° C.

The other examples listed in the table below were prepared analogously to Example 1(a).

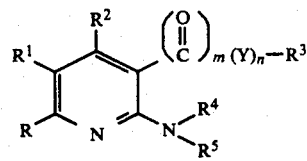

(m and n = 0 and $R^3$ = H for all the following Examples)

| Example No. | R | $R^1$ | $R^2$ | $R^4$ | $R^5$ | Recrystallised from solvent | M.p. °C. | Yield in % of theory |
|---|---|---|---|---|---|---|---|---|
| 3 | $CH_3$ | –⟨○⟩–NMe₂ | –⟨○⟩–Cl | (–C₂H₄)₂N– | ⟨○⟩ | dimethyl-sulphoxide | 191–192 | 50 |
| 4 | $CH_3$ | –⟨○⟩–F | –⟨○⟩–F | (–C₂H₄)₂N– | ⟨○⟩ | methanol | 155–156 | 57 |
| 5 | $CH_3$ | –⟨○⟩ | –⟨○⟩ | (–C₂H₄)₂N– | ⟨○⟩ | dimethyl-sulphoxide | 151–152 | 75 |
| 6 | $CH_3$ | furyl | furyl | (–C₂H₄)₂N– | ⟨○⟩ | ethyl acetate/ether × 2 HCl | 230° C. | 79 |
| 7 | $CH_3$ | –⟨○⟩–CH₃ | –⟨○⟩–CH₃ | –(CH₂)₄– | | acetone/ether × 1 HCl | 205–206 | 72 |

Among the new 2-amino-pyridine derivative salts of the invention, those salts that are acid-addition salts and are pharmaceutically acceptable are particularly important and are preferred.

The new free 2-amino pyridine derivatives of the formula (I) and their salts can be interconverted in any suitable manner; methods for such interconversion are known in the art.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

For the purposes of this specification the term 'pharmaceutically acceptable bioprecursor' of an active compound of the invention means a compound having a structural formula different from the active compound but which nonetheless, upon administration to an animal is converted in the animal's body to the active compound.

What is claimed is:

1. A compound of the formula I

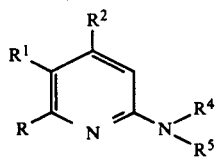

or a salt thereof in which

R represents an alkyl group having 1 to 4 carbon atoms or a benzyl or phenyl group, $R^1$ and $R^2$ are identical or different and each represents a furyl or phenyl group, the phenyl ring optionally containing 1 or 2 identical or different substituents selected from fluorine, chlorine, trifluoromethyl, trifluoromethoxy, trifluoromethylthio, hydroxy, alkyl having 1 to 4 carbon atoms, alkoxy or alkylthio having 1 to 4 carbon atoms an alkylamino having 1 or 2 carbon atoms per alkyl radical and $R^4$ and $R^5$ together with a nitrogen atom, form a piperazine ring which is optionally substituted in the 4-position by the substituents defined above for $R_2$.

2. A compound according to claim 1 which is 4,5-bis(4-hydroxyphenyl)-6-methyl-2-(4-phenylpiperazino)-pyridine.

3. A compound according to claim 1 which is 4-(4-chlorophenyl)-5-(dimethylaminophenyl)-6-methyl-2-(4-phenylpiperazino)-pyridine.

4. A compound according to claim 1 which is 4,5-bisphenyl-6-methyl-2-(4-phenylpiperazino)-pyridine.

5. A pharmaceutical composition containing as an active ingredient an effective amount of a compound according to claim 1 in admixture with an inert pharmaceutical carrier.

6. A pharmaceutical composition of claim 5 in the form of a sterile or physiologically isotonic aqeous solution.

7. A composition according to claim 5 or 6 containing from 0.5 to 95% by weight of the said active ingredient.

8. A medicament in dosage unit form comprising an effective amount of a compound according to claim 1 and an inert pharmaceutical carrier.

9. A medicament of claim 8 in the form of tablets, pills, dragees, capsules, ampoules, or suppositories.

10. A method of combating diseases involving fat metabolism in warm-blooded animals which comprises administering to the animals an effective amount of an active compound according to to claim 1 ether alone or in admixture with a diluent or in the form of a medicament.

11. A method according to claim 10 in which the active compound is administered in an amount of 1 to 500 mg per kg body weight per day.

12. A method according to claim 10 or 11 in which the active compound is administered orally.

* * * * *